United States Patent [19]

Legoux et al.

[11] Patent Number: 5,856,142

[45] Date of Patent: *Jan. 5, 1999

[54] METHOD FOR THE EXTRACTION OF PERIPLASMIC PROTEINS FROM PROKARYOTIC MICROORGANISMS IN THE PRESENCE OF ARGININE

[75] Inventors: Richard Legoux, Le Faget; Paul Maldonado, St. Symphorien D'Ozon; Marc Salome, Castanet Tolosan, all of France

[73] Assignee: Sanofi, Paris, France

[ * ] Notice: The term of this patent shall not extend beyond the expiration date of Pat. No. 5,700,665.

[21] Appl. No.: 906,957

[22] Filed: Aug. 6, 1997

Related U.S. Application Data

[63] Continuation of Ser. No. 594,469, Jan. 31, 1996, Pat. No. 5,700,665.

[30] Foreign Application Priority Data

Jan. 31, 1995 [FR] France .................................. 95 01083

[51] Int. Cl.⁶ ............................... C12N 1/21; C12P 21/00

[52] U.S. Cl. .................... 435/71.2; 435/69.4; 435/69.52; 435/252.3

[58] Field of Search .............................. 435/69.1, 69.52, 435/71.1, 71.2, 243, 244, 252.1, 252.3, 252.33, 69.4

*Primary Examiner*—George C. Elliot
*Assistant Examiner*—Robert Schwartzman
*Attorney, Agent, or Firm*—Bacon & Thomas

[57] ABSTRACT

The invention relates to a method for the extraction of recombinant periplasmic proteins wherein arginine is used as the extraction agent. In particular, the invention relates to a method for the extraction of a periplasmic protein of interest, which essentially consists in:

(i) suspending the pellet of cells or of cell debris from cells, which cells originate from the culture of a prokaryotic microorganism transformed with an expression vector containing a gene coding for the said protein and means for its expression in the periplasm of the said microorganism, in a buffer solution containing arginine; and (ii) recovering the protein of interest in the supernatant of the bacterial suspension thereby obtained.

18 Claims, No Drawings

METHOD FOR THE EXTRACTION OF PERIPLASMIC PROTEINS FROM PROKARYOTIC MICROORGANISMS IN THE PRESENCE OF ARGININE

This application is a Continuation of application Ser. No. 08/594,469, filed Jan. 31, 1996, now U.S. Pat. No. 5,700,665.

The present invention relates to the extraction of recombinant proteins produced by prokaryotic microorganisms, especially by *E. coli*.

Increasing use is being made of genetic engineering techniques for the production of proteins of interest such as, for example, insulin, inter-leukins, growth hormone, and the like.

Generally, the microorganism is transformed with an expression vector containing a gene coding for the protein of interest and means needed for its expression such as the regulator signals. The micro-organism is then cultured on a suitable culture medium and according to suitable culture parameters and, when a sufficient number of microorganism cells has been arrived at, the addition of an inducer triggers the so-called expression phase, during which the desired protein is produced at high level and accumulates. On completion of culturing, the cells in suspension are separated from the culture medium, for example by centrifugation or microfiltration, and are then subjected to an extraction method which frequently begins with an operation of disrupting of the walls of the microorganisms.

The expression of a gene coding for a protein of interest in a prokaryotic microorganism can be cytoplasmic, periplasmic or secretory, depending on the nature of the means of expression employed with the said gene (promoter, terminator, ribosome binding site, signal peptide, and the like).

Cytoplasmic expression enables large amounts of proteins to be obtained. However, prior to the extraction of the protein of interest, it is necessary, for proteins comprising one or more disulphide bridges, to carry out a step of denaturation/renaturation, which represents an especially cumbersome and intricate step during production on an industrial scale. The denaturation/renaturation step is carried out according to traditional means well known to a person skilled in the art, using a denaturing agent in the presence of a reducing agent followed by renaturation conditions comprising, in particular, a monitoring of the redox state of the solution. Among denaturing agents used, most particular mention must be made of guanidine hydrochloride, which has been proposed in a method for obtaining human interleukin-2. To this end, reference may be made, for example, to the document EP-A2-0,145,390.

With Gram-negative bacteria, little or no use has been made of secretory expression systems in which the protein of interest is to be found actively in the culture medium, on account of their low productivity. It should be noted here that the medium of a bacterial culture at high density in a bioreactor is not an ideal residence place for sensitive recombinant proteins on account, for example, of the risks of interfacial denaturation.

Periplasmic expression enables recombinant proteins which are, in principle, correctly folded to be obtained directly in a space protected from the environment and, as a result, represents a judicious choice for obtaining proteins, in particular unglycosylated proteins. In this case, it is hence not necessary to subject the proteins to a denaturation/renaturation step.

The methods of cell disruption generally used in this field are, for example, cell lysis by sonication or by mechanical pressure (French Pressure Cell, ball mill), chemical lysis or enzymatic lysis, osmotic shock and treatment using chaotropic agents or detergents. These methods disrupt the majority of cell membranes, including the plasma membranes and membranes of the endoplasmic reticulum, to form a homogeneous suspension of cell debris. The nature of the pellet of cell debris which can be harvested in general after centrifugation (nuclei, cytoskeleton, mitochondria, lysosomes, ribosomes, macromolecules, and the like) is dependent especially on the time and the speed of centrifugation (10 minutes at 1000 g to 3 hours at 150,000 g).

The difficulties encountered during the extraction operations vary according to the type of expression and the extraction methods used, and are, in particular:

loss in yield of the recombinant protein loss of biological activity of the recombinant protein proteolytic degradation of the recombinant protein toxicity of the extraction agents and obligatory monitoring of their removal difficulty of industrial implementation mixing of the periplasmic proteins with cytoplasmic proteins.

Furthermore, when the proteins of interest produced are hydrophobic or charged, they may associate with cell components which are themselves hydrophobic or charged, thereby rendering extraction especially difficult.

Considerable benefit might accrue from undertaking the industrial production of recombinant proteins of interest by genetic engineering, but this necessitates the development of extraction methods which avoid or minimize the above drawbacks.

In effect, it is not only important to produce large amounts of protein of interest, but these proteins must also not be contaminated with the extraction agents and must retain their full biological activity.

Various methods have been proposed for this purpose, especially for the extraction/separation of interleukin-2.

The document EP-A2-0,145,390 describes a method for obtaining unglycosylated human interleukin-2 (IL-2) having a specific activity of greater than 104 U/mg, which employs a step of separation by column chromatography to extract the IL-2. This method also involves a denaturation step using guanidine hydrochloride.

The document EP-A2-0,147,819 proposes a method for obtaining homogeneous and pure recombinant interleukin-2. This method consists in culturing a microorganism transformed by means of an expression vector containing the gene coding for interleukin-2, in causing lysis of the cells, in recovering the cell debris, in extracting the IL-2 by washing the cell debris with a suitable washing solution and then in purifying the washinng solution by chromatography. The washing solutions used can contain a salt such as sodium chloride or guanidine hydrochloride, or a detergent such as, for example, the product known under the trade name "Triton X®-100".

According to a preferred variant, the successive use of three washing solutions, namely a washing solution containing sodium chloride, a washing solution containing a detergent and a washing solution containing guanidine hydrochloride, is recommended.

The document EP-A1-0,337,243 describes a method for purifying human interleukin-2 which utilizes a system of two reversed-phase liquid chromatography columns. Before the step of purification by chromatography, the insoluble fraction of the bacterial cell lysate is extracted with a solution containing guanidine hydrochloride to obtain a bacterial extract, which is then diluted using a guanidine hydrochloride-free buffer and thereafter chromatographed, elution being carried out with an acetonitrile gradient.

It has now been found, surprisingly, that the extraction of a protein of interest produced by a prokaryotic microorganism, transformed with an expression vector containing a gene coding for the protein of interest and means for its expression such as the regulator signals needed for its periplasmic expression, may be carried out by suspending the pellet of cells or of cell debris from the microorganism, originating from the culture of the said microorganism, in a buffer solution, the said solution advantageously containing arginine, it being possible for the arginine to be in the L and/or D form.

According to a first aspect, the subject of the invention is the use of arginine as an agent for the extraction of periplasmic proteins.

According to another aspect, the subject of the present invention is a method for the extraction of a periplasmic protein of interest, which consists in:

1) suspending the pellet of cells originating from the culture of a microorganism, transformed with an expression vector containing a gene coding for the said protein and all the regulator signals needed for its periplasmic expression, in a buffer solution containing arginine and, after a period of contact under appropriate pH, temperature, bacterial concentration, and the like, conditions, 2) recovering the protein of interest in the supernatant of the bacterial suspension thereby obtained.

A variant of the said method for the extraction of a periplasmic protein of interest consists in suspending the pellet of cell debris, obtained after lysis of the cells originating from the culture, in the buffer solution containing arginine.

Extraction of the periplasmic proteins is especially efficient when the extraction buffer consists of an aqueous solution containing arginine at a concentration equal to at least 0.4M arginine within the limit of solubility of arginine at room temperature in water (in the region of 0.8M in pure water and above this in the presence of salts), and when its pH is slightly alkaline, preferably equal to 8.

Arginine is a natural a-amino acid which has been proposed as an auxiliary agent for the denaturation/renaturation/substitution of two chains of Abbokinase® (urinary plasminogen activator), in which chains a native peptide is partially replaced by a synthetic peptide during this operation. To this end, reference may be made to the paper by GA. Homandberg and T. Wai in Biochimica et Biophysica Acta, 1990, 1038, 209–215.

In the method of the invention or its variant, denaturation/renaturation of the protein is not carried out and the arginine participates only in respect of the extraction of a protein from a pellet of cells or of cell debris from microorganisms.

Arginine brings about noteworthy effects on the extraction of the protein, in respect of both the yield and the biological activity of the protein. It was, in effect, found that, for example, the mature form of IL-13 is recovered with the method of the invention in yields of greater than 95% while retaining the biological activity of the molecule. It should be noted that trials of extraction by osmotic shock on the same expression system do not lead to comparable yields.

Comparative trials showed that guanidine.HCl used under the same conditions also enables the IL-13 protein to be recovered in a yield of greater than 95% but, in contrast, the biological activity of the protein thus recovered is impaired more than by the arginine method.

While it is not wished to limit interpretation to some particular theory, arginine is thought to act as a mild and biological chaotropic agent, as opposed to the powerful chaotropic agents which are denaturing at the high concentrations needed, equal to or greater than 5M, in order to effect extraction, such as guanidine hydrochloride.

The method of the invention or its variant may be carried out following any method of culture of a microorganism transformed with an expression vector containing a gene coding for the protein of interest and means for a periplasmic expression of the said protein, such as all the necessary regulator signals.

It is obvious to a person skilled in the art that the method is applicable to bacteria closely related to *E. coli,* that is to say to so-called facultative anaerobic Gram-negative bacteria which constitute the Enterobacteriaceae group. In this family Enterobacteriaceae, the following species are to be found in particular: *Escherichia, Salmonella, Erwinia* and also *Shigella, Klebsiella, Serratia, Proteus* and *Enterobacter.*

Bearing in mind the chaotropic character of arginine, it is also apparent that arginine can, depending on the case, advantageously substitute for other chaotropic agents. Without it being possible to exemplify on all the families of bacteria on account of the diversity of the living systems in question, a person skilled in the art will know how to apply and adapt the arginine extraction method to his particular case.

Such culture methods are well known to a person skilled in the art. Methods describing the fermenter culture of Gram-negative bacteria are described, for example, in Patent EP-360,641 and EP-356,335 reporting the obtaining and use of the *E. coli* strains known as SEBR 1250 and TP 2339.

When the desired number of cells has been arrived at, the culture is subjected to a centrifugation (in general) or a microfiltration, and the pellet of biomass obtained is brought into contact with a buffer solution containing arginine according to the method of the invention.

As a general rule, the procedure is performed at a temperature between room temperature of approximately 25° C. and 2° C., preferably at 4° C.

The contact time of the cell pellet with the buffer solution containing arginine must be sufficient to permit passage of the protein of interest into the buffer solution.

In general, when the procedure is performed at 4° C., the contact time is advantageously approximately 1 hour.

The extraction, that is to say passage of the periplasmic protein into the medium, continues during the period of contact of the biomass and the arginine-containing extraction buffer. The contact time providing for complete extraction or an extraction showing no further change in level is between 30 minutes and 16 hours. Trials show that satisfactory extraction yields may be obtained in the space of a few hours at a temperature of 4° C. It has also been noted that gentle stirring of the biomass in its extraction buffer so as to avoid sedimentation of the pellet of microorganisms gives superior results, that is to say higher levels of extraction as a function of time.

The extraction method according to the invention is suitable for extracting both hydrophobic proteins such as, for example, interleukins, especially IL-13 described in the document EP-A1-0,506,574, and hydrophilic proteins such as, for example, growth hormone (hGH). The method of the invention simplifies the obtaining of hGH, which normally necessitates the use of an osmotic shock for its extraction.

To carry out the extraction of the protein of interest directly on the suspension of the cell pellet, a buffer solution containing arginine at a concentration of between 0.4M and 0.8M will be preferred.

When it is desired to carry out the extraction of the periplasmic protein of interest on the pellet of cell debris according to the variant of the method of the invention, the procedure is the same as is used in the method of the invention up to the step of obtaining the cell pellet obtained after centrifugation or micro-filtration, and disruption of the cells is then performed according to methods well known to a person skilled in the art. Methods of cell disruption are described, for example, in C. T. Choma and H. Yamazaki, Can. J. Microbiol., 1981, 27, 547–550; L. O. Ingram, Journal of Bacteriology, 1981, 146, 1, 331–336; N. G. Nossal and L. A. Heppel, Journal of Biological Chemistry, 1966, 241, 13, 3065–3072; R. Bennett, D. R. Taylor and A. Hurst, Biochem. Biophys. Acta, 18(3), 512–521 (1966), and in the collective work Fermentation and enzyme technology, Chap. 12, 239–309, J. Wiley and Sons publishers (1979).

The pellet of cell debris harvested, as a general rule, after centrifugation is resuspended and then brought into contact with a buffer solution containing arginine. The contact time of the suspension of cell debris with the buffer solution containing arginine must be sufficient to permit passage of the protein of interest into the buffer solution. In general, for a temperature of 4° C., the contact time providing for almost complete extraction is 48 hours. Similarly, it was noted that gentle stirring of the biomass in its extraction buffer, thereby avoiding sedimentation of the cell debris, gives higher levels of extraction as a function of time.

This variant of the extraction method according to the invention is suitable for extracting especially periplasmic proteins of interest which are strongly associated with the cell membranes, such as, for example, interleukins.

It is well known to a person skilled in the art that the extraction buffer containing arginine according to the invention may also contain an auxiliary detergent which will have the effect of improving the yield and/or the rate of extraction of the protein of interest. Among auxiliary detergents which may be used, a person skilled in the art will be able to choose from those which enable the advantages of using arginine as extraction agent, especially the retention of the biological activity of the protein of interest, to be preserved. Among these mild auxiliary detergents, there may be mentioned, for example, alkyl glycosides such as alkyl maltosides, nonyl α- or β-D-glycopyranosides, octyl α- or β-D-glycopyranosides or alkylcarbamoylmethyl α- or β-D-glycopyranosides such as, for example, Hecameg®, the very low toxicity of which suggests the possibility of allowing it to appear in trace amounts as formulation agent in the final product.

To carry out the extraction of the protein of interest from the suspension of the pellet of cell debris, it will be preferable to use a buffer solution containing arginine at a concentration of between 0.4M and 2.5M, it being possible for a concentration of 2.5M arginine to be obtained especially in the presence of salts.

Moreover, it was found that arginine exerts a considerable beneficial effect on the yields of secreted recombinant periplasmic protein if it is added at unfamiliar concentrations much higher than those encountered in the culture media manufactured from commercial protein hydrolysates, and which enable the arginine requirements of the strain employed to be covered.

Furthermore, it was found that the beneficial effect exerted by arginine is especially considerable if the arginine concentrations added to the culture medium are between 2 g/l and 10 g/l.

Thus, according to another aspect, the subject of the present invention is a method for the culture of a prokaryotic microorganism transformed by means of an expression vector containing a gene coding for a protein of interest, which consists in culturing the said microorganism in the presence of arginine at a concentration equal to at least 2 g/l, and especially at a concentration of between 2 g/l and 10 g/l.

A person skilled in the art will optimize this arginine concentration for each particular case.

This method is especially suitable for the production of proteins having activity of the cytokine type, especially IL-13, as described in the document EP-A1-0,506,574.

The invention will now be described in greater detail by means of the EXAMPLES below, given only by way of illustration.

EXAMPLE 1

Extraction of periplasmic IL-13 from *E. coli* in the presence of arginine on cell pellet.

1/ Flask culture:

In this example, *E. coli* strain RB 791 (Roger Brent, PNAS 78 (1981) pp. 4204–4208), transformed with the plasmid p922 obtained according to methods similar to those defined in Patents EP 360,641 and 356,335 and whose DNA sequence is the sequence SEQ ID NO:1, was used.

The different sequences which constitute this plasmid p922 are shown below.

PROMOTER SEQUENCE (SEQ ID NO:2)

The hexanucleotides TTGCTT and TATAAT characteristic of the promoters in *E. coli* are shown in bold characters

|     | XhoI | | | | |
|-----|------|---|---|---|---|
| 1   | TCGAGTGGGT | TTGAGGCGAT | CACACTTCTG | TTAACGCAGA | ACCTAAACGC |
| 51  | ATCTCGACTG | CACGGTGCAC | CAATGCTTCT | GGCGTCAGGC | AGCCATCGGA |
| 101 | AGCTGTGGTA | TGGCTGTGCA | GGTCGTAAAT | CACTGCATAA | TTCGTGTCGC |
| 151 | TCAAGGCGCA | CTCCCGTTCT | GGATAATGTT | TTTTGCGCCG | ACATCATAAC |
| 201 | GGTTCTGGCA | AATATTCTGA | AATGAGCTGT | TTCGAGCTGA | CTGACTGTTG −35 |
| 251 | CTTATATTAC | ATCGATAGCG | TATAATGTGT | GG | |

SEQUENCE OF THE UNTRANSLATED 5-PRIME REGION OF THE MESSENGER (SEQ ID NO:3)

The ribosome binding site is shown in bold characters. The sequence CAT located at the 3-prime end of this sequence is a portion of the hexanucleotide recognized by the restriction enzyme Nde I

```
                                                    RBS
283  AATTGTGAGC  GGATAACAAT  TTCACACAGT  TTTTCGCGAA  GAAGGAGATA

333  TACAT
```

SEQUENCE CODING FOR THE IL-13 PRECURSOR (SEQ ID NO:4)

The sequence in italics corresponds to the sequence of mature IL-13. The sequence which is not in bold characters is a linker sequence linking the end of the sequence coding for IL-13 to the hexanucleotide recognized by the restriction enzyme BamH I

```
338  ATGAAAAGAA  TCCTGGCGTT  AGCTGCGCTG  ACTACCGTTG  TATTCTCTGC

388  GTCCGCCTTC  GCTGGCCCTG  TGCCTCCCAG  TACTGCCCTC  AGGGAGCTCA

438  TTGAGGAGCT  GGTCAACATC  ACCCAGAACC  AGAAGGCTCC  GCTCTGCAAT

488  GGCAGCATGG  TATGGAGCAT  CAACCTGACA  GCTGGCATGT  ACTGTGCAGC

538  CCTGGAATCC  CTGATCAACG  TGTCAGGCTG  CAGTGCCATC  GAGAAGACCC

588  AGAGGATGCT  GAGCGGATTC  TGCCCGCACA  AGGTCTCAGC  TGGGCAGTTT

638  TCCAGCTTGC  ATGTCCGAGA  CACCAAAATC  GAGGTGGCCC  AGTTTGTAAA

688  GGACCTGCTC  TTACATTTAA  AGAAACTTTT  TCGCGAGGGA  CGGTTCAACT

738  GAAACTTCGA  AAGCATCATT  ATTTG
```

TERMINATION SEQUENCES (SEQ ID NO:5)

```
763  GGATCCGGCT  GCTAACAAAG  CCCGAAAGGA  AGCTGAGTTG  GCTGCTGCCA
```

PHAGE T7 GENE 10 TERMINATOR (SEQ ID NO:6)

```
813  CCGCTGAGCA  ATAACTAGCA  TAACCCCTTG  GGGCCTCTAA     ACGGGTCTTG

HindIII
863  AGGGGTTTTT  TGCTGAAAGG  AGGAACTATA  TCCGGATGTA  CCAAGCTTGG

913  CCGGATCAAA  GTTTTGTCGT  CTTTCCAGAC  GTTAGTAAAT  GAATTTTCTG

963  TATGAGGTTT  TGCTAAACAA  CTTTCAACAG  TTTCAGCGGA  GTGAGAATAG
```

PHAGE fd TERMINATOR (SEG ID NO:7)

```
1013 AAAGGAACAA  CTAAAGGAAT  TGCGAATAAT  AATTTTTTCA    CGTTGAAAAT

1063 CTCCAAAAAA  AAAGGCTCCA  AAAGGAGCCT  TTAATTGTAT  CGGTTTATCA
```

| | | -continued | | |
|---|---|---|---|---|
| 1113 GCTTGCTTTC | GAGGTGAATT | TCTTAAACAG | CTTGATACCG | ATAGTTGCGC |
| 1163 CGACAATGAC | AACAACCATC | GCCCACGCAT | AACCGATATA | TTCGGTCGCT |
| 1213 GAGGCTTGCA | GGGAGTCAAA | GGCCGCTTTT | GCGGGATCGA | T |

GENE CODING FOR THE LACTOSE OPERON REPRESSOR (SEQ ID NO:8)

SacII
| 1254 CCGCGGAAGC | ATAAAGTGTA | AAGCCTGGGG | TGCCTAATGA | GTGAGCTAAC |
|---|---|---|---|---|
| 1304 TCACATTAAT | TGCGTTGCGC | TCACTGCCCG | CTTTCCAGTC | GGGAAACCTG |
| 1354 TCGTGCCAGC | TGCATTAATG | AATCGGCCAA | CGCGCGGGGA | GAGGCGGTTT |
| 1404 GCGTATTGGG | CGCCAGGGTG | GTTTTTCTTT | TCACCAGTGA | GACGGGCAAC |
| 1454 AGCTGATTGC | CCTTCACCGC | CTGGCCCTGA | GAGAGTTGCA | GCAAGCGGTC |
| 1504 CACGCTGGTT | TGCCCCAGCA | GGCGAAAATC | CTGTTTGCTG | GTGGTTAACG |
| 1554 GCGGGATATA | ACATGAGCTG | TCTTCGGTAT | CGTCGTATCC | CACTACCGAG |
| 1604 ATATCCGCAC | CAACGCGCAG | CCCGGACTCG | GTAATGGCGC | GCATTGCGCC |
| 1654 CAGCGCCATC | TGATCGTTGG | CAACCAGCAT | CGCAGTGGGA | ACGATGCCCT |
| 1704 CATTCAGCAT | TTGCATGGTT | TGTTGAAAAC | CGGACATGGC | ACTCCAGTCG |
| 1754 CCTTCCCGTT | CCGCTATCGG | CTGAATTTGA | TTGCGAGTGA | GATATTTATG |
| 1804 CCAGCCAGCC | AGACGCAGAC | GCGCCGAGAC | AGAACTTAAT | GGGCCCGCTA |
| 1854 ACAGCGCGAT | TTGCTGGTGA | CCCAATGCGA | CCAGATGCTC | CACGCCCAGT |
| 1904 CGCGTACCGT | CTTCATGGGA | GAAAATAATA | CTGTTGATGG | GTGTCTGGTC |
| 1954 AGAGACATCA | AGAAATAACG | CCGGAACATT | AGTGCAGGCA | GCTTCCACAG |
| 2004 CAATGGCATC | CTGGTCATCC | AGCGGATAGT | TAATGATCAG | CCCACTGACG |
| 2054 CGTTGCGCGA | GAAGATTGTG | CACCGCCGCT | TTACAGGCTT | CGACGCCGCT |
| 2104 TCGTTCTACC | ATCGACACCA | CCACGCTGGC | ACCCAGTTGA | TCGGCGCGAG |
| 2154 ATTTAATCGC | CGCGACAATT | TGCGACGGCG | CGTGCAGGGC | CAGACTGGAG |
| 2204 GTGGCAACGC | CAATCAGCAA | CGACTGTTTG | CCCGCCAGTT | GTTGTGCCAC |
| 2254 GCGGTTGGGA | ATGTAATTCA | GCTCCGCCAT | CGCCGCTTCC | ACTTTTTCCC |
| 2304 GCGTTTTCGC | AGAAACGTGG | CTGGCCTGGT | TCACCACGCG | GGAAACGGTC |
| 2354 TGATAAGAGA | CACCGGCATA | CTCTGCGACA | TCGTATAACG | TTACTGGTTT |
| 2404 CACATTCACC | ACCCTGAATT | GACTCTCTTC | CGGGCGCTAT | CATGCCATAC |
| 2454 CGCGAAAGGT | TTTGCGCCAT | TCGATCTACG | CCGGACGCAT | CGTGGCCGCA |

SEQUENCE OF pBR 327 (SEQ ID NO:9)

```
       PflmI
2506  CCAACCCTTG  GCAGAACATA  TCCATCGCGT  CCGCCATCTC  CAGCAGCCGC

2556  ACGCGGCGCA  TCTCGGGCCG  CGTTGCTGGC  GTTTTTCCAT  AGGCTCCGCC

2606  CCCCTGACGA  GCATCACAAA  AATCGACGCT  CAAGTCAGAG  GTGGCGAAAC

2656  CCGACAGGAC  TATAAAGATA  CCAGGCGTTT  CCCCCTGGAA  GCTCCCTCGT

2706  GCGCTCTCCT  GTTCCGACCC  TGCCGCTTAC  CGGATACCTG  TCCGCCTTTC

2756  TCCCTTCGGG  AAGCGTGGCG  CTTTCTCAAT  GCTCACGCTG  TAGGTATCTC

2806  AGTTCGGTGT  AGGTCGTTCG  CTCCAAGCTG  GGCTGTGTGC  ACGAACCCCC

2856  CGTTCAGCCC  GACCGCTGCG  CCTTATCCGG  TAACTATCGT          CTTGAGTCCA

2906  ACCCGGTAAG  ACACGACTTA  TCGCCACTGG  CAGCAGCCAC  TGGTAACAGG

2956  ATTAGCAGAG  CGAGGTATGT  AGGCGGTGCT  ACAGAGTTCT  TGAAGTGGTG

3006  GCCTAACTAC  GGCTACACTA  GAAGGACAGT  ATTTGGTATC  TGCGCTCTGC

3056  TGAAGCCAGT  TACCTTCGGA  AAAAGAGTTG  GTAGCTCTTG  ATCCGGCAAA

3106  CAAACCACCG  CTGGTAGCGG  TGGTTTTTTT  GTTTGCAAGC  AGCAGATTAC

3156  GCGCAGAAAA  AAAGGATCTC  AAGAAGATCC  TTTGATCTTT  TCTACGGGGT

3206  CTGACGCTCA  GTGGAACGAA  AACTCACGTT  AAGGGATTTT  GGTCATGAGA

3256  TTATCAAAAA  GGATCTTCAC  CTAGATCCTT  TTAAATTAAA  AATGAAGTTT

3306  TAAATCAATC  TAAAGTATAT  ATGAGTAAAC  TTGGTCTGAC  AGTTACCAAT

3356  GCTTAATCAG  TGAGGCACCT  ATCTCAGCGA  TCTGTCTATT  TCGTTCATCC

3406  ATAGTTGCCT  GACTCCCCGT  CGTGTAGATA  ACTACGATAC  GGGAGGGCTT

3456  ACCATCTGGC  CCCAGTGCTG  CAATGATACC  GCGAGACCCA  CGCTCACCGG

3506  CTCCAGATTT  ATCAGCAATA  AACCAGCCAG  CCGGAAGGGC  CGAGCGCAGA

3556  AGTGGTCCTG  CAACTTTATC  CGCCTCCATC  CAGTCTATTA  ATTGTTGCCG

3606  GGAAGCTAGA  GTAAGTAGTT  CGCCAGTTAA  TAGTTTGCGC  AACGTTGTTG

3656  CCATTGCTGC  AGGCATCGTG  GTGTCACGCT  CGTCGTTTGG  TATGGCTTCA

3706  TTCAGCTCCG  GTTCCCAACG  ATCAAGGCGA  GTTACATGAT  CCCCCATGTT

3756  GTGCAAAAAA  GCGGTTAGCT  CCTTCGGTCC  TCCGATCGTT  GTCAGAAGTA

3806  AGTTGGCCGC  AGTGTTATCA  CTCATGGTTA  TGGCAGCACT  GCATAATTCT
```

-continued

| | | | | |
|---|---|---|---|---|
| 3856 CTTACTGTCA | TGCCATCCGT | AAGATGCTTT | TCTGTGACTG | GTGAGTACTC |
| 3906 AACCAAGTCA | TTCTGAGAAT | AGTGTATGCG | GCGACCGAGT | TGCTCTTGCC |
| 3956 CGGCGTCAAC | ACGGGATAAT | ACCGCGCCAC | ATAGCAGAAC | TTTAAAAGTG |
| 4006 CTCATCATTG | GAAAACGTTC | TTCGGGGCGA | AAACTCTCAA | GGATCTTACC |
| 4056 GCTGTTGAGA | TCCAGTTCGA | TGTAACCCAC | TCGTGCACCC | AACTGATCTT |
| 4106 CAGCATCTTT | TACTTTCACC | AGCGTTTCTG | GGTGAGCAAA | AACAGGAAGG |
| 4156 CAAAATGCCG | CAAAAAAGGG | AATAAGGGCG | ACACGGAAAT | GTTGAATACT |
| 4206 CATACTCTTC | CTTTTTCAAT | ATTATTGAAG | CATTTATCAG | GGTTATTGTC |
| 4256 TCATGAGCGG | ATACATATTT | GAATGTATTT | AGAAAAATAA | ACAAATAGGG |
| 4306 GTTCCGCGCA | CATTTCCCCG | AAAAGTGCCA | CCTGACGTCT | AAGAAACCAT |
| 4356 TATTATCATG | ACATTAACCT | ATAAAAATAG | GCGTATCACG | AGGCCCTTTC |

4406 GTCCC (Plasmid pBR 327 is described in Gene, 9, 287–305 (1980))

This strain E. coli RB 791/p922 was set up in preculture overnight at 30° C. with stirring at 200 rpm on L medium (Luria broth described in Molecular Cloning, A Laboratory Manual Sambrook, Fritsch, Maniatis; Cold Spring Harbor Laboratory Press, 2nd edition 1989) containing 100 mg/l of ampicillin. From this preculture, a further flask of L medium was inoculated such that the initial OD (OD=optical density at 600 nm, OD=1 corresponds to 400–450 mg biomass/liter) was 0.6. After waiting for one hour, the culture was induced with 1 mM IPTG (isopropyl β-D-1-thiogalactopyranoside) and culturing was continued for 3 hours. The samples of the bacterial suspension were centrifuged and the bacterial pellets thus recovered were suspended in the extraction buffers below, such that the final OD was 10, this being equivalent to 4.5 g biomass/liter, at the time of extraction.

The extraction buffers used in this example are the following:
A: 0.8M arginine pH 8.0 corrected with HCl in Milli-Q® water (Millipore)
B: 5M guanidine.HCl in Milli-Q® water without pH correction.

Extraction was performed in 1 hour at 4° C. with gentle magnetic stirring.

To measure the efficiency of extraction, samples equivalent to 1 ml of culture suspension with an OD of 0.2 were removed, and the corresponding bacterial pellets obtained by centrifugation at 5,000 g for 10 min were applied to 16.5% polyacrylamide gel after denaturation with SDS. The bacterial suspensions were also centrifuged and their supernatants were desalted by ultrafiltration (Millipore Ultrafree-MC filtration device with a cut-off threshold of 5,000 Da) before being applied to gel. The gel itself was visualized by Western blotting using an anti-CHO IL-13 antibody and quantified with a PhosphorImager® (Molecular Dynamics). The anti-CHO (Chinese hamster ovary) IL-13 antibody used in this example was obtained by immunizing rabbits.

It was found in this example that extraction in the presence of guanidine.HCl or alternatively in the presence of arginine is virtually complete for the mature form, with extraction yields greater than 99% in both cases. It was also noted that, in the supernatant extracted in the presence of arginine, the precursor form of IL-13 is not seen, in distinction to the extract obtained in the presence of guanidine.HCl.

2/ Fermenter culture:

E. coli strain RB 791/p922 was set up on L medium with 100 mg/l ampicillin and incubated at 30° C. with stirring to constitute a preculture. A 100 ml volume of this preculture was used as inoculum for an MBR brand fermenter of total volume 2.5 liters. Culturing was performed in a volume of 1.2 liters on a medium whose composition is given below and under the conditions defined below.

Medium for fermenter—E. coli strain RB 791/p922

The formula is given for 1 liter final, the volume of the inoculum is to be subtracted.

1. Dissolve in 700 ml of Milli-O® water:

| Component | Mass/liter |
|---|---|
| EDTA | 1 g |
| FeSO$_4$.7H$_2$O | 45 mg |
| MgSO$_4$.7H$_2$O | 1.5 g |
| K$_2$SO$_4$ | 0.75 g |
| CaCl$_2$.2H$_2$O | 32 mg |
| NaCl | 1.45 g |
| KCl | 5 g |
| HY-SOY ® | 75 g |
| L-methionine | 1.4 g |
| Tryptophan | 1 g |
| Trace elements* | 2 ml |
| Yeast extract | 10 g |

Make to 800 ml with Milli-Q® water, autoclave 30 min at 120° C.

2. Filter through 0.2 μm in 100 ml of Milli-Q® water:

| | |
|---|---|
| Glycerol | 15 g |
| K$_2$HPO$_4$ | 7.1 g |

The glycerol concentration will be maintained at between 10 and 15 g/l during culture.

3. At the time of induction add:

| | |
|---|---|
| IPTG | 1 g |
| 6-Aminocaproic acid | 0.65 g |
| HY-SOY ® | 40 g |
| L-cysteine | 0.3 g |

The volume of this addition is not included in the other calculations.

Solution of trace elements
This is used in the proportion of 1 ml/liter.
For 1 liter of Milli-Q® water final, dissolve in 800 ml:

| | mass/l |
|---|---|
| H$_3$BO$_3$ | 3 mg |
| NaMoO$_4$.2H$_2$O | 4.8 mg |
| MnSO$_4$.H$_2$O | 59 mg |
| CoCl$_2$.6H$_2$O | 23.8 mg |
| CuSO$_4$.5H$_2$O | 8.7 mg |
| ZnSO$_4$.7H$_2$O | 13 mg |
| AlCl$_3$.6H$_2$O | 60 mg |
| KCr(SO$_4$)$_2$.12H$_2$O | 6 mg |
| KI (added at the time of use) | 60 mg |
| NiSO$_4$.6H$_2$O | 2.6 mg |

Add 100 ml of concentrated HCl. Make to 1000 ml with Milli-Q® water.

When the OD has reached 58, the expression of IL-13 is triggered by the addition of IPTG at a concentration of 1 g/l and continued for 5 hours.

The fermenter culture parameters were as follows:

pH=7.4

T=30° C.

pO$_2$=40 mm Hg regulated by stirring, with a flow rate of air of between 1 and 3 liters/min.

The methods of extraction and of measurement of the biological activity which are applied are the same as those described in section 1 above.

It is found that extraction—on a bacterial pellet obtained in a fermenter, no longer in a flask—in the presence of guanidine.HCl or alternatively in the presence of arginine is virtually complete for the mature form of IL-13, with extraction yields of greater than 97% in both cases.

EXAMPLE 2

Biological activity of the IL-13 thus extracted

The extracts obtained in the presence of guanidine.HCl or of arginine in Example 1 were desalted by ultrafiltration as described above. After serial dilution, they were brought into contact with an IL-13-dependent subclone of the B9 cell line. The IL-13 activity of the diluted samples induces the growth of B9 cells, and the half-proliferation concentration was determined. Cell growth was stopped after 3 days of contact by adding MTT (3-(4,5-dimethylthiazol-2-yl)-2,5-diphenyltetrazolium bromide), and measured in a spectrophotometer by the absorption of the blue colouration produced at 565 nm. The IL-13 biological activity was expressed in ng/ml relative to an IL-13 standard which was itself calibrated against the candidate international standard, obtained from an CHO IL-13 culture, obtained by immunizing rabbits according to N. Vita, Archives of Biochemistry and Biophysics, 1983, 225, 2, 436–445.

The results obtained appear in TABLE II below.

TABLE II

| Trial on B9 cell line | IL-13 in ng/ml | Biological activity in ng/ml | Specific biological activity |
|---|---|---|---|
| Control | 500 | 500 | 100 |
| Arginine | 3,200 | 1,376 | 43 |
| Guanidine | 4,300 | 1,098 | 25 |

The above results show that the specific biological activity of the arginine extract is, before any other subsequent purification operation, greater than that of the guanidine hydrochloride extract.

EXAMPLE 3

Extraction of periplasmic hGH from *E. coli* in the presence of arginine on cell pellet The strain SEBR 1250 (EP-360,641 and EP-356,335) was set up in preculture overnight at 37° C. with stirring at 200 rpm on L medium (Luria broth) containing 100 mg/l of ampicillin. From this preculture, a further flask of L medium was inoculated such that the initial OD was 0.2. After waiting for one hour, the culture was induced with 1 mM IPTG and culturing was continued for 3 hours. The samples of the bacterial suspension were centrifuged, and the bacterial pellets thus recovered were suspended in the extraction buffers such that the final OD was 10, this being equivalent to ~4.5 g biomass/liter, at the time of extraction.

The extraction conditions were as follows:

| Chaotropic agent | pH | T | time |
|---|---|---|---|
| 0.8 M Arginine | 8.0 | 22° C. | 20 hours |
| 0.8 M Arginine | 8.0 | 4° C. | 20 hours |

To measure the efficacy of extraction, samples equivalent to 1 ml of culture suspension with an OD of 0.2 were removed, and the corresponding bacterial pellets obtained by centrifugation at 5,000 g for 10 minutes were applied to 16.5% polyacrylamide gel after denaturation with SDS. The bacterial suspensions were also centrifuged and their supernatants applied to gel. The gel itself was visualized by Western blotting using an anti-hGH antibody, and quantified with a PhosphorImager® (Molecular Dynamics). The anti-hGH antibodies used were obtained by immunizing rabbits.

Analysis of the bands obtained with the PhosphorImager® enables the conclusion to be drawn that the extraction of human periplasmic hGH produced in *E. coli* in the presence of arginine is efficient. In this example, a yield of at least 60% may be achieved in the presence of 0.8M arginine, pH 8.0, T 22° C. and a period of 20 hours, and an extraction yield of greater than 80% may be achieved in the presence of 0.8M arginine, pH 8.0, T 4° C. and a period of 20 hours.

Since hGH is a hydrophilic protein, it may be concluded from this that recombinant proteins differing greatly in nature, accumulated in the periplasm of *E. coli,* may be extracted simply in the presence of arginine.

EXAMPLE 4

Extraction of periplasmic IL-13 from *E. coli* on cell debris in the presence of arginine 1/ Fermenter culture In this example, *E. coli* strain TP2339 (EP 360,641 and EP 356,335), transformed with plasmid p922 obtained according to methods similar to those defined in EXAMPLE 1 was used.

*E. coli* strain TP2339/p922 was set up on L medium with 100 mg/l ampicillin and incubated at 30° C. with stirring to constitute a preculture. A 100 ml volume of this preculture was used as inoculum for an MBR® brand fermenter of total volume 2.5 liters. Culturing was performed in a volume of 1.2 liters in a medium and under conditions defined below.

Medium for fermenter—*E. coli* strain TP2339/p922

Calculated for a final volume of 1.2 liters, the culture medium consists of the addition of one liter of autoclaved phase and 0.1 liter of filtered phase whose compositions are described below, and of 0.1 liter of preculture defined above.

1/ Autoclaved phase (1000 ml):

Dissolve in 900 ml of Milli-Q® water:

|  | Mass/l |
| --- | --- |
| Tricine | 360 mg |
| $FeSO_4.7H_2O$ | 280 mg |
| $CaCl_2.2H_2O$ | 6.7 mg |
| $MgCl_2.6H_2O$ | 1.27 g |
| $K_2SO_4$ | 8.71 g |
| NaCl | 500 mg |
| KCl | 5 g |
| Hy-Case (SF) ® | 25 g |
| Yeast extract | 18 g |
| Trace elements* | 1 ml |
| L-arginine | 1.5 g |

Adjust the pH to 7.4 with KOH solution and then make to 1000 ml with Milli-Q® water. Autoclave 30 minutes at 120° C.

2/ Filtered phase (100 ml)

Filter under sterile conditions through a 0.2 $\mu$m membrane:

| Glucose | 20 g |
| --- | --- |
| Glycerol | 50 g |
| $K_2HPO_4$ | 5 g |

The glucose concentration will be maintained during culturing at a concentration of between 5 and 15 g/l.

When the OD has reached 40 (approximately 16 g of dry matter/liter), the expression of IL-13 is triggered by the addition of IPTG at a concentration of 1 g/l and continued for 5 hours. The culture parameters were as follows:

pH=7.4 regulated with 3N HCl and KOH

T=37° C.

$pO_2$=50 mbar regulated by stirring, with a flow rate of air of between 1 and 3 liters/min.

2/ Recovery and grinding of the bacterial bodies

One liter of culture suspension is centrifuged for 20 minutes at ~6400 g. The pellet is taken up in the same volume of 10 mM Tris buffer, 1 mM EDTA, 1 mg/l pepstatin, pH 8, with mechanical stirring using a propeller-type paddle.

Grinding is accomplished in a Manton-Gaulin press at a pressure of 700 bars in two runs. The ground preparation as it is may be stored at −80° C. in this example.

3/ Extraction

After thawing, 5 ml of the ground preparation with an OD equal to 75 (30 g of dry matter/liter) are removed and then centrifuged for 50 minutes at 23,300 g.

The pellet thereby obtained is taken up in one third of the initial volume with 0.1 mM Tris buffer, pH 7.0, and then made to the initial volume with a solution containing arginine such that the final arginine concentration is 2.5M and the pH 8.0.

For this example, an auxiliary detergent (Hecameg® at a final concentration of 20 g/l) was combined with the arginine.

The suspension of cell debris made up in this way is placed at 4° C. on a rotary stirrer at 300 rpm for 2 days.

The suspension is then centrifuged a final time for 50 minutes at 23,300 g, the supernatant constituting the expected extract.

4/ Biochemical analysis and analysis of biological activity a) Assay of total proteins was performed by the Biorad® "Protein Assay" method.

b) The method of assay of recombinant IL-13 is that used in Example 1.

Yield of IL-13 thus extracted: the results obtained are described in the following table:

|  | In the suspension of cell debris before extraction | In the supernatant after extraction |
| --- | --- | --- |
| Total proteins | 324 $\mu$g/ml | 108 $\mu$g/ml |
| Recombinant IL-13 | 575 ng/ml | 390 ng/ml |

It was found in this example that the extraction carried out on cell debris in the presence of 2.5M arginine and an auxiliary detergent enabled an extraction yield of approximately 70% to be obtained.

EXAMPLE 5

Expression of IL-13 in the presence of arginine in the culture medium

*E. coli* strain RB 791/p922 was cultured on L medium with 100 mg/l ampicillin in the presence of different concentrations of arginine. Induction was triggered 1 hour after inoculation by the addition of 1 mM IPTG, and culturing was continued for 3 hours.

The samples of bacterial pellets—equivalent to 1 ml of culture suspension with an OD of 0.2—and the corresponding samples of supernatant were applied to gel, visualized and quantified as described above. The results are given in the table below:

| Sample | OD end of culture | IL-13 in ng/l OD 1 |
| --- | --- | --- |
| Control | 1.17 | 388 |
| Arginine 2 g/l | 1.24 | 455 |
| Arginine 4 g/l | 1.24 | 600 |
| Arginine 8 g/l | 1 | 720 |

It is apparent that, under the experimental conditions and in the expression system in question:

arginine increases the expression of periplasmic IL-13 from 2 g/l, and substantially from 4 g/l, growth of the bacterium is slowed down at a concentration of 8 g/l at these concentrations, arginine does not cause leakage of IL-13 into the supernatant.

The value of the arginine extraction method according to the invention is the ability to use protein extracts as they are or with a minimum of treatment in tests of biological activity.

This simplification of the extraction method affords an advantage both for the industrial production of recombinant periplasmic proteins, and for screening by assaying the biological activity on the laboratory scale in relation, for example, to mutated proteins.

In distinction to guanidine.HCl, frequently used as extraction agent, arginine does not attack the materials employed in industry, in particular steels. Furthermore, arginine is a non-polluting agent, which thus does not require an expensive effluent treatment process.

The value of expressing a periplasmic protein in the presence of arginine at concentrations equal to at least 2 g/l, and especially at concentrations of between 2 g/l and 10 g/l, in the culture medium is demonstrated by the increase in the yield of secreted recombinant protein obtained in vivo.

We claim:

1. A method for the extraction of a periplasmic protein of interest, which comprises the steps of
    (i) culturing a Gram-negative bacterium transformed with an expression vector containing a gene coding for said protein of interest and means for a periplasmic expression thereof,
    (ii) subjecting the resulting culture to centrifugation or microfiltration thereby producing a cell pellet,
    (iii) suspending the resulting cell pellet in buffer solution containing arginine thereby producing a suspension,
    (iv) centrifuging the resulting suspension thereby producing a supernatant, and
    (v) recovering the protein of interest from the supernatant thereby obtained.

2. The method according to claim 1, wherein the buffer solution containing arginine is an alkaline aqueous solution having an arginine concentration of at least 0.4M.

3. The method according to claim 1, wherein the protein of interest is IL-13.

4. The method according to claim 1, wherein the protein of interest is hGH.

5. The method according to claim 2, wherein the arginine concentration is between 0.4M and 0.8M.

6. The method according to claim 2, wherein the protein of interest is IL-13.

7. The method according to claim 2, wherein the protein of interest is hGH.

8. The method according to claim 5, wherein the protein of interest is IL-13.

9. The method according to claim 5, wherein the protein of interest is hGH.

10. A method for the extraction of a periplasmic protein of interest, which comprises the steps of:
    (i) culturing a Gram-negative bacterium transformed with an expression vector containing a gene coding for said protein of interest and means for a periplasmic expression thereof,
    (ii) subjecting the resulting culture to centrifugation or microfiltration thereby producing a cell pellet,
    (iii) lysing the cells from the cell pellet thereby obtained and centrifuging the resulting lysate thereby producing a pellet of cell debris,
    (iv) suspending the pellet of cell debris thereby obtained in a buffer solution containing arginine thereby producing a suspension,
    (v) centrifuging the resulting suspension thereby producing a supernatant, and
    (vi) recovering the protein of interest from the supernatant thereby obtained.

11. The method according to claim 10, wherein the buffer solution containing arginine is an alkaline aqueous solution having an arginine concentration of at least 0.4M.

12. The method according to claim 10, wherein the protein of interest is IL-13.

13. The method according to claim 10, wherein the protein of interest is hGH.

14. The method according to claim 11, wherein the arginine concentration is between 0.4M and 2.5M.

15. The method according to claim 11, wherein the protein of interest is IL-13.

16. The method according to claim 11, wherein the protein of interest is hGH.

17. The method according to claim 14, wherein the protein of interest is IL-13.

18. The method according to claim 14, wherein the protein of interest is hGH.

* * * * *

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 4410 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 1:

```
TCGAGTGGGT  TTGAGGCGAT  CACACTTCTG  TTAACGCAGA  ACCTAAACGC  ATCTCGACTG        60

CACGGTGCAC  CAATGCTTCT  GGCGTCAGGC  AGCCATCGGA  AGCTGTGGTA  TGGCTGTGCA       120

GGTCGTAAAT  CACTGCATAA  TTCGTGTCGC  TCAAGGCGCA  CTCCCGTTCT  GGATAATGTT       180

TTTTGCGCCG  ACATCATAAC  GGTTCTGGCA  AATATTCTGA  AATGAGCTGT  TTCGAGCTGA       240

CTGACTGTTG  CTTATATTAC  ATCGATAGCG  TATAATGTGT  GGAATTGTGA  GCGGATAACA       300

ATTTCACACA  GTTTTTCGCG  AAGAAGGAGA  TATACATATG  AAAAAGATCC  TGGCGTTAGC       360

TGCGCTGACT  ACCGTTGTAT  TCTCTGCGTC  CGCCTTCGCT  GGCCCTGTGC  CTCCCAGTAC       420

TGCCCTCAGG  GAGCTCATTG  AGGAGCTGGT  CAACATCACC  CAGAACCAGA  AGGCTCCGCT       480

CTGCAATGGC  AGCATGGTAT  GGAGCATCAA  CCTGACAGCT  GGCATGTACT  GTGCAGCCCT       540

GGAATCCCTG  ATCAACGTGT  CAGGCTGCAG  TGCCATCGAG  AAGACCCAGA  GGATGCTGAG       600

CGGATTCTGC  CCGCACAAGG  TCTCAGCTGG  GCAGTTTTCC  AGCTTGCATG  TCCGAGACAC       660

CAAAATCGAG  GTGGCCCAGT  TTGTAAAGGA  CCTGCTCTTA  CATTTAAAGA  AACTTTTTCG       720

CGAGGGACGG  TTCAACTGAA  ACTTCGAAAG  CATCATTATT  TGGGATCCGG  CTGCTAACAA       780

AGCCCGAAAG  GAAGCTGAGT  TGGCTGCTGC  CACCGCTGAG  CAATAACTAG  CATAACCCCT       840

TGGGGCCTCT  AAACGGGTCT  TGAGGGGTTT  TTTGCTGAAA  GGAGGAACTA  TATCCGGATG       900

TACCAAGCTT  GGCCGGATCA  AAGTTTTGTC  GTCTTCCAG   ACGTTAGTAA  ATGAATTTTC       960

TGTATGAGGT  TTTGCTAAAC  AACTTTCAAC  AGTTTCAGCG  GAGTGAGAAT  AGAAAGGAAC      1020

AACTAAAGGA  ATTGCGAATA  ATAATTTTTT  CACGTTGAAA  ATCTCCAAAA  AAAAAGGCTC      1080

CAAAAGGAGC  CTTTAATTGT  ATCGGTTTAT  CAGCTTGCTT  TCGAGGTGAA  TTTCTTAAAC      1140

AGCTTGATAC  CGATAGTTGC  GCCGACAATG  ACAACAACCA  TCGCCCACGC  ATAACCGATA      1200

TATTCGGTCG  CTGAGGCTTG  CAGGGAGTCA  AAGGCCGCTT  TTGCGGGATC  GATCCGCGGA      1260

AGCATAAAGT  GTAAAGCCTG  GGGTGCCTAA  TGAGTGAGCT  AACTCACATT  AATTGCGTTG      1320

CGCTCACTGC  CCGCTTTCCA  GTCGGGAAAC  CTGTCGTGCC  AGCTGCATTA  ATGAATCGGC      1380
```

```
CAACGCGCGG GGAGAGGCGG TTTGCGTATT GGGCGCCAGG GTGGTTTTTC TTTTCACCAG  1440
TGAGACGGGC AACAGCTGAT TGCCCTTCAC CGCCTGGCCC TGAGAGAGTT GCAGCAAGCG  1500
GTCCACGCTG GTTTGCCCCA GCAGGCGAAA ATCCTGTTTG CTGGTGGTTA ACGGCGGGAT  1560
ATAACATGAG CTGTCTTCGG TATCGTCGTA TCCCACTACC GAGATATCCG CACCAACGCG  1620
CAGCCCGGAC TCGGTAATGG CGCGCATTGC GCCCAGCGCC ATCTGATCGT TGGCAACCAG  1680
CATCGCAGTG GGAACGATGC CCTCATTCAG CATTTGCATG GTTTGTTGAA AACCGGACAT  1740
GGCACTCCAG TCGCCTTCCC GTTCCGCTAT CGGCTGAATT TGATTGCGAG TGAGATATTT  1800
ATGCCAGCCA GCCAGACGCA GACGCGCCGA GACAGAACTT AATGGGCCCG CTAACAGCGC  1860
GATTTGCTGG TGACCCAATG CGACCAGATG CTCCACGCCC AGTCGCGTAC CGTCTTCATG  1920
GGAGAAAATA ATACTGTTGA TGGGTGTCTG GTCAGAGACA TCAAGAAATA ACGCCGGAAC  1980
ATTAGTGCAG GCAGCTTCCA CAGCAATGGC ATCCTGGTCA TCCAGCGGAT AGTTAATGAT  2040
CAGCCCACTG ACGCGTTGCG CGAGAAGATT GTGCACCGCC GCTTTACAGG CTTCGACGCC  2100
GCTTCGTTCT ACCATCGACA CCACCACGCT GGCACCCAGT TGATCGGCGC GAGATTTAAT  2160
CGCCGCGACA ATTTGCGACG GCGCGTGCAG GGCCAGACTG GAGGTGGCAA CGCCAATCAG  2220
CAACGACTGT TTGCCCGCCA GTTGTTGTGC CACGCGGTTG GGAATGTAAT TCAGCTCCGC  2280
CATCGCCGCT TCCACTTTTT CCCGCGTTTT CGCAGAAACG TGGCTGGCCT GGTTCACCAC  2340
GCGGGAAACG GTCTGATAAG AGACACCGGC ATACTCTGCG ACATCGTATA ACGTTACTGG  2400
TTTCACATTC ACCACCCTGA ATTGACTCTC TTCCGGGCGC TATCATGCCA TACCGCGAAA  2460
GGTTTTGCGC CATTCGATCT ACGCCGGACG CATCGTGGCC GCAAACCAAC CCTTGGCAGA  2520
ACATATCCAT CGCGTCCGCC ATCTCCAGCA GCCGCACGCG GCGCATCTCG GGCCGCGTTG  2580
CTGGCGTTTT TCCATAGGCT CCGCCCCCCT GACGAGCATC ACAAAAATCG ACGCTCAAGT  2640
CAGAGGTGGC GAAACCCGAC AGGACTATAA AGATACCAGG CGTTTCCCCC TGGAAGCTCC  2700
CTCGTGCGCT CTCCTGTTCC GACCCTGCCG CTTACCGGAT ACCTGTCCGC CTTTCTCCCT  2760
TCGGGAAGCG TGGCGCTTTC TCAATGCTCA CGCTGTAGGT ATCTCAGTTC GGTGTAGGTC  2820
GTTCGCTCCA AGCTGGGCTG TGTGCACGAA CCCCCCGTTC AGCCCGACCG CTGCGCCTTA  2880
TCCGGTAACT ATCGTCTTGA GTCCAACCCG GTAAGACACG ACTTATCGCC ACTGGCAGCA  2940
GCCACTGGTA ACAGGATTAG CAGAGCGAGG TATGTAGGCG GTGCTACAGA GTTCTTGAAG  3000
TGGTGGCCTA ACTACGGCTA CACTAGAAGG ACAGTATTTG GTATCTGCGC TCTGCTGAAG  3060
CCAGTTACCT TCGGAAAAAG AGTTGGTAGC TCTTGATCCG GCAAACAAAC CACCGCTGGT  3120
AGCGGTGGTT TTTTGTTTG  CAAGCAGCAG ATTACGCGCA GAAAAAAGG  ATCTCAAGAA  3180
GATCCTTTGA TCTTTTCTAC GGGGTCTGAC GCTCAGTGGA ACGAAAACTC ACGTTAAGGG  3240
ATTTTGGTCA TGAGATTATC AAAAAGGATC TTCACCTAGA TCCTTTTAAA TTAAAAATGA  3300
AGTTTTAAAT CAATCTAAAG TATATATGAG TAAACTTGGT CTGACAGTTA CCAATGCTTA  3360
ATCAGTGAGG CACCTATCTC AGCGATCTGT CTATTTCGTT CATCCATAGT TGCCTGACTC  3420
CCCGTCGTGT AGATAACTAC GATACGGGAG GGCTTACCAT CTGGCCCCAG TGCTGCAATG  3480
ATACCGCGAG ACCCACGCTC ACCGGCTCCA GATTTATCAG CAATAAACCA GCCAGCCGGA  3540
AGGGCCGAGC GCAGAAGTGG TCCTGCAACT TTATCCGCCT CCATCCAGTC TATTAATTGT  3600
TGCCGGGAAG CTAGAGTAAG TAGTTCGCCA GTTAATAGTT TGCGCAACGT TGTTGCCATT  3660
GCTGCAGGCA TCGTGGTGTC ACGCTCGTCG TTTGGTATGG CTTCATTCAG CTCCGGTTCC  3720
CAACGATCAA GGCGAGTTAC ATGATCCCCC ATGTTGTGCA AAAAAGCGGT TAGCTCCTTC  3780
```

-continued

| | | | | | |
|---|---|---|---|---|---|
| GGTCCTCCGA | TCGTTGTCAG | AAGTAAGTTG | GCCGCAGTGT | TATCACTCAT | GGTTATGGCA | 3840
| GCACTGCATA | ATTCTCTTAC | TGTCATGCCA | TCCGTAAGAT | GCTTTTCTGT | GACTGGTGAG | 3900
| TACTCAACCA | AGTCATTCTG | AGAATAGTGT | ATGCGGCGAC | CGAGTTGCTC | TTGCCCGGCG | 3960
| TCAACACGGG | ATAATACCGC | GCCACATAGC | AGAACTTTAA | AAGTGCTCAT | CATTGGAAAA | 4020
| CGTTCTTCGG | GGCGAAAACT | CTCAAGGATC | TTACCGCTGT | TGAGATCCAG | TTCGATGTAA | 4080
| CCCACTCGTG | CACCCAACTG | ATCTTCAGCA | TCTTTTACTT | TCACCAGCGT | TTCTGGGTGA | 4140
| GCAAAAACAG | GAAGGCAAAA | TGCCGCAAAA | AAGGGAATAA | GGGCGACACG | GAAATGTTGA | 4200
| ATACTCATAC | TCTTCCTTTT | TCAATATTAT | TGAAGCATTT | ATCAGGGTTA | TTGTCTCATG | 4260
| AGCGGATACA | TATTTGAATG | TATTTAGAAA | AATAAACAAA | TAGGGGTTCC | GCGCACATTT | 4320
| CCCCGAAAAG | TGCCACCTGA | CGTCTAAGAA | ACCATTATTA | TCATGACATT | AACCTATAAA | 4380
| AATAGGCGTA | TCACGAGGCC | CTTTCGTCCC | | | | 4410

( 2 ) INFORMATION FOR SEQ ID NO: 2:

( i ) SEQUENCE CHARACTERISTICS:
        ( A ) LENGTH: 282 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 2:

| | | | | | |
|---|---|---|---|---|---|
| TCGAGTGGGT | TTGAGGCGAT | CACACTTCTG | TTAACGCAGA | ACCTAAACGC | ATCTCGACTG | 60
| CACGGTGCAC | CAATGCTTCT | GGCGTCAGGC | AGCCATCGGA | AGCTGTGGTA | TGGCTGTGCA | 120
| GGTCGTAAAT | CACTGCATAA | TTCGTGTCGC | TCAAGGCGCA | CTCCGTTCT | GGATAATGTT | 180
| TTTTGCGCCG | ACATCATAAC | GGTTCTGGCA | AATATTCTGA | AATGAGCTGT | TTCGAGCTGA | 240
| CTGACTGTTG | CTTATATTAC | ATCGATAGCG | TATAATGTGT | GG | | 282

( 2 ) INFORMATION FOR SEQ ID NO: 3:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 3:

| | | | | | |
|---|---|---|---|---|---|
| AATTGTGAGC | GGATAACAAT | TTCACACAGT | TTTTCGCGAA | GAAGGAGATA | TACAT | 55

( 2 ) INFORMATION FOR SEQ ID NO: 4:

( i ) SEQUENCE CHARACTERISTICS:
        ( A ) LENGTH: 425 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 4:

| | | | | | |
|---|---|---|---|---|---|
| ATGAAAAGA | TCCTGGCGTT | AGCTGCGCTG | ACTACCGTTG | TATTCTCTGC | GTCCGCCTTC | 60
| GCTGGCCCTG | TGCCTCCCAG | TACTGCCCTC | AGGGAGCTCA | TTGAGGAGCT | GGTCAACATC | 120
| ACCCAGAACC | AGAAGGCTCC | GCTCTGCAAT | GGCAGCATGG | TATGGAGCAT | CAACCTGACA | 180

-continued

| | | | | | |
|---|---|---|---|---|---|
|GCTGGCATGT|ACTGTGCAGC|CCTGGAATCC|CTGATCAACG|TGTCAGGCTG|CAGTGCCATC|240
|GAGAAGACCC|AGAGGATGCT|GAGCGGATTC|TGCCCGCACA|AGGTCTCAGC|TGGGCAGTTT|300
|TCCAGCTTGC|ATGTCCGAGA|CACCAAAATC|GAGGTGGCCC|AGTTTGTAAA|GGACCTGCTC|360
|TTACATTTAA|AGAAACTTTT|TCGCGAGGGA|CGGTTCAACT|GAAACTTCGA|AAGCATCATT|420
|ATTTG| | | | |425

( 2 ) INFORMATION FOR SEQ ID NO: 5:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 5:

| | | | | |
|---|---|---|---|---|
|GGATCCGGCT|GCTAACAAAG|CCCGAAAGGA|AGCTGAGTTG|GCTGCTGCCA|50

( 2 ) INFORMATION FOR SEQ ID NO: 6:

( i ) SEQUENCE CHARACTERISTICS:
    ( A ) LENGTH: 200 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 6:

| | | | | | |
|---|---|---|---|---|---|
|CCGCTGAGCA|ATAACTAGCA|TAACCCCTTG|GGGCCTCTAA|ACGGGTCTTG|AGGGGTTTTT|60
|TGCTGAAAGG|AGGAACTATA|TCCGGATGTA|CCAAGCTTGG|CCGGATCAAA|GTTTTGTCGT|120
|CTTTCCAGAC|GTTAGTAAAT|GAATTTTCTG|TATGAGGTTT|TGCTAAACAA|CTTTCAACAG|180
|TTTCAGCGGA|GTGAGAATAG| | | |200

( 2 ) INFORMATION FOR SEQ ID NO: 7:

( i ) SEQUENCE CHARACTERISTICS:
    ( A ) LENGTH: 241 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 7:

| | | | | | |
|---|---|---|---|---|---|
|AAAGGAACAA|CTAAAGGAAT|TGCGAATAAT|AATTTTTTCA|CGTTGAAAAT|CTCCAAAAAA|60
|AAAGGCTCCA|AAAGGAGCCT|TTAATTGTAT|CGGTTTATCA|GCTTGCTTTC|GAGGTGAATT|120
|TCTTAAACAG|CTTGATACCG|ATAGTTGCGC|CGACAATGAC|AACAACCATC|GCCCACGCAT|180
|AACCGATATA|TTCGGTCGCT|GAGGCTTGCA|GGGAGTCAAA|GGCCGCTTTT|GCGGGATCGA|240
|T| | | | |241

( 2 ) INFORMATION FOR SEQ ID NO: 8:

( i ) SEQUENCE CHARACTERISTICS:
    ( A ) LENGTH: 1252 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO: 8:

| | | | | | | |
|---|---|---|---|---|---|---|
| CCGCGGAAGC | ATAAAGTGTA | AAGCCTGGGG | TGCCTAATGA | GTGAGCTAAC | TCACATTAAT | 60 |
| TGCGTTGCGC | TCACTGCCCG | CTTTCCAGTC | GGGAAACCTG | TCGTGCCAGC | TGCATTAATG | 120 |
| AATCGGCCAA | CGCGCGGGGA | GAGGCGGTTT | GCGTATTGGG | CGCCAGGGTG | GTTTTTCTTT | 180 |
| TCACCAGTGA | GACGGGCAAC | AGCTGATTGC | CCTTCACCGC | CTGGCCCTGA | GAGAGTTGCA | 240 |
| GCAAGCGGTC | CACGCTGGTT | TGCCCCAGCA | GGCGAAAATC | CTGTTTGCTG | GTGGTTAACG | 300 |
| GCGGGATATA | ACATGAGCTG | TCTTCGGTAT | CGTCGTATCC | CACTACCGAG | ATATCCGCAC | 360 |
| CAACGCGCAG | CCCGGACTCG | GTAATGGCGC | GCATTGCGCC | CAGCGCCATC | TGATCGTTGG | 420 |
| CAACCAGCAT | CGCAGTGGGA | ACGATGCCCT | CATTCAGCAT | TTGCATGGTT | TGTTGAAAAC | 480 |
| CGGACATGGC | ACTCCAGTCG | CCTTCCCGTT | CCGCTATCGG | CTGAATTTGA | TTGCGAGTGA | 540 |
| GATATTTATG | CCAGCCAGCC | AGACGCAGAC | GCGCCGAGAC | AGAACTTAAT | GGGCCCGCTA | 600 |
| ACAGCGCGAT | TTGCTGGTGA | CCCAATGCGA | CCAGATGCTC | CACGCCCAGT | CGCGTACCGT | 660 |
| CTTCATGGGA | GAAAATAATA | CTGTTGATGG | GTGTCTGGTC | AGAGACATCA | AGAAATAACG | 720 |
| CCGGAACATT | AGTGCAGGCA | GCTTCCACAG | CAATGGCATC | CTGGTCATCC | AGCGGATAGT | 780 |
| TAATGATCAG | CCCACTGACG | CGTTGCGCGA | GAAGATTGTG | CACCGCCGCT | TTACAGGCTT | 840 |
| CGACGCCGCT | TCGTTCTACC | ATCGACACCA | CCACGCTGGC | ACCCAGTTGA | TCGGCGCGAG | 900 |
| ATTTAATCGC | CGCGACAATT | TGCGACGGCG | CGTGCAGGGC | CAGACTGGAG | GTGGCAACGC | 960 |
| CAATCAGCAA | CGACTGTTTG | CCCGCCAGTT | GTTGTGCCAC | GCGGTTGGGA | ATGTAATTCA | 1020 |
| GCTCCGCCAT | CGCCGCTTCC | ACTTTTTCCC | GCGTTTTCGC | AGAAACGTGG | CTGGCCTGGT | 1080 |
| TCACCACGCG | GGAAACGGTC | TGATAAGAGA | CACCGGCATA | CTCTGCGACA | TCGTATAACG | 1140 |
| TTACTGGTTT | CACATTCACC | ACCCTGAATT | GACTCTCTTC | CGGGCGCTAT | CATGCCATAC | 1200 |
| CGCGAAAGGT | TTTGCGCCAT | TCGATCTACG | CCGGACGCAT | CGTGGCCGCA | AA | 1252 |

( 2 ) INFORMATION FOR SEQ ID NO: 9:

( i ) SEQUENCE CHARACTERISTICS:
      ( A ) LENGTH: 1905 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO: 9:

| | | | | | | |
|---|---|---|---|---|---|---|
| CCAACCCTTG | GCAGAACATA | TCCATCGCGT | CCGCCATCTC | CAGCAGCCGC | ACGCGGCGCA | 60 |
| TCTCGGGCCG | CGTTGCTGGC | GTTTTTCCAT | AGGCTCCGCC | CCCCTGACGA | GCATCACAAA | 120 |
| AATCGACGCT | CAAGTCAGAG | GTGGCGAAAC | CCGACAGGAC | TATAAAGATA | CCAGGCGTTT | 180 |
| CCCCCTGGAA | GCTCCCTCGT | GCGCTCTCCT | GTTCCGACCC | TGCCGCTTAC | CGGATACCTG | 240 |
| TCCGCCTTTC | TCCCTTCGGG | AAGCGTGGCG | CTTTCTCAAT | GCTCACGCTG | TAGGTATCTC | 300 |
| AGTTCGGTGT | AGGTCGTTCG | CTCCAAGCTG | GGCTGTGTGC | ACGAACCCCC | CGTTCAGCCC | 360 |
| GACCGCTGCG | CCTTATCCGG | TAACTATCGT | CTTGAGTCCA | ACCCGGTAAG | ACACGACTTA | 420 |
| TCGCCACTGG | CAGCAGCCAC | TGGTAACAGG | ATTAGCAGAG | CGAGGTATGT | AGGCGGTGCT | 480 |
| ACAGAGTTCT | TGAAGTGGTG | GCCTAACTAC | GGCTACACTA | GAAGGACAGT | ATTTGGTATC | 540 |
| TGCGCTCTGC | TGAAGCCAGT | TACCTTCGGA | AAAAGAGTTG | GTAGCTCTTG | ATCCGGCAAA | 600 |
| CAAACCACCG | CTGGTAGCGG | TGGTTTTTTT | GTTTGCAAGC | AGCAGATTAC | GCGCAGAAAA | 660 |
| AAAGGATCTC | AAGAAGATCC | TTTGATCTTT | TCTACGGGGT | CTGACGCTCA | GTGGAACGAA | 720 |

-continued

| | | | | | | |
|---|---|---|---|---|---|---|
| AACTCACGTT | AAGGGATTTT | GGTCATGAGA | TTATCAAAAA | GGATCTTCAC | CTAGATCCTT | 780 |
| TTAAATTAAA | AATGAAGTTT | TAAATCAATC | TAAAGTATAT | ATGAGTAAAC | TTGGTCTGAC | 840 |
| AGTTACCAAT | GCTTAATCAG | TGAGGCACCT | ATCTCAGCGA | TCTGTCTATT | TCGTTCATCC | 900 |
| ATAGTTGCCT | GACTCCCCGT | CGTGTAGATA | ACTACGATAC | GGGAGGGCTT | ACCATCTGGC | 960 |
| CCCAGTGCTG | CAATGATACC | GCGAGACCCA | CGCTCACCGG | CTCCAGATTT | ATCAGCAATA | 1020 |
| AACCAGCCAG | CCGGAAGGGC | CGAGCGCAGA | AGTGGTCCTG | CAACTTTATC | CGCCTCCATC | 1080 |
| CAGTCTATTA | ATTGTTGCCG | GGAAGCTAGA | GTAAGTAGTT | CGCCAGTTAA | TAGTTTGCGC | 1140 |
| AACGTTGTTG | CCATTGCTGC | AGGCATCGTG | GTGTCACGCT | CGTCGTTTGG | TATGGCTTCA | 1200 |
| TTCAGCTCCG | GTTCCCAACG | ATCAAGGCGA | GTTACATGAT | CCCCCATGTT | GTGCAAAAAA | 1260 |
| GCGGTTAGCT | CCTTCGGTCC | TCCGATCGTT | GTCAGAAGTA | AGTTGGCCGC | AGTGTTATCA | 1320 |
| CTCATGGTTA | TGGCAGCACT | GCATAATTCT | CTTACTGTCA | TGCCATCCGT | AAGATGCTTT | 1380 |
| TCTGTGACTG | GTGAGTACTC | AACCAAGTCA | TTCTGAGAAT | AGTGTATGCG | GCGACCGAGT | 1440 |
| TGCTCTTGCC | CGGCGTCAAC | ACGGGATAAT | ACCGCGCCAC | ATAGCAGAAC | TTTAAAAGTG | 1500 |
| CTCATCATTG | GAAAACGTTC | TTCGGGGCGA | AAACTCTCAA | GGATCTTACC | GCTGTTGAGA | 1560 |
| TCCAGTTCGA | TGTAACCCAC | TCGTGCACCC | AACTGATCTT | CAGCATCTTT | TACTTTCACC | 1620 |
| AGCGTTTCTG | GGTGAGCAAA | AACAGGAAGG | CAAAATGCCG | CAAAAAAGGG | AATAAGGGCG | 1680 |
| ACACGGAAAT | GTTGAATACT | CATACTCTTC | CTTTTTCAAT | ATTATTGAAG | CATTTATCAG | 1740 |
| GGTTATTGTC | TCATGAGCGG | ATACATATTT | GAATGTATTT | AGAAAAATAA | ACAAATAGGG | 1800 |
| GTTCCGCGCA | CATTTCCCCG | AAAAGTGCCA | CCTGACGTCT | AAGAAACCAT | TATTATCATG | 1860 |
| ACATTAACCT | ATAAAAATAG | GCGTATCACG | AGGCCCTTTC | GTCCC | | 1905 |